United States Patent [19]
Schwan

[11] 3,959,293
[45] May 25, 1976

[54] METHYL 1-(3,4-DICHLOROBENZYL)-2,3-DIOXOISONIPECOTATE

[75] Inventor: Thomas J. Schwan, Norwich, N.Y.

[73] Assignee: Morton-Norwich Products, Inc., Norwich, N.Y.

[22] Filed: Apr. 3, 1975

[21] Appl. No.: 564,609

Related U.S. Application Data

[63] Continuation-in-part of Ser. No. 509,334, Sept. 26, 1974, abandoned.

[52] U.S. Cl. .................... 260/293.76; 260/293.86; 424/267
[51] Int. Cl.² ......................................... C07D 211/42

[58] Field of Search ............................. 260/293.76

[56] References Cited
UNITED STATES PATENTS
3,423,414    1/1969    Blatter ............................ 260/243 B OTHER PUBLICATIONS
Hasse et al., C.A. 54: 22568a, (1960).
Hasse et al., C.A. 56: 12746c, (1962).
Carroll et al., J. Org. Chem. 31: 2960–2961, (1966).

*Primary Examiner*—Sherman D. Winters
*Attorney, Agent, or Firm*—Anthony J. Franze

[57] ABSTRACT

The title compound is a useful antifungal agent.

1 Claim, No Drawings

METHYL 1-(3,4-DICHLOROBENZYL)-2,3-DIOXOISONIPECOTATE

This application is a continuation-in-part of my copending application Ser. No. 509,334 filed Sept. 26, 1974 now abandoned.

This invention is concerned with the chemical compound methyl 1-(3,4-dichlorobenzyl)-2,3-dioxoisonipecotate. It is a useful antifungal agent. It is fungicidal to agar cultures of *Microsporum canis*, *Trichophyton mentagrophytes*, *Microsporum audouini*, and *Trichophyton tonsurans* within fifteen minutes at a concentration of two percent in polyethylene glycol 400. At a concentration of 0.02% in 50% ethanol it inhibits the growth of *Candida albicans* and *Microsporum canis* in the commonly employed agar diffusion test. It is adapted to be combined in various forms such as elixirs, dusts, unguents, solutions and suspensions to provide compositions inimical to fungal growth.

In order that this invention may be readily available to and understood by those skilled in the art, the currently preferred method for its preparation is briefly described:

To a mixture of 51.3 g (0.30 mole) of methyl 2,3-dioxoisonipecotate, m.p. 155°–156° prepared by transesterification of ethyl 2,3-dioxoisonipecotate, in 1000 ml toluene was added 24 g sodium hydride-60% in mineral oil (i.e., 14.4 g, 0.60 mole). The mixture was stirred and refluxed for 1.5 hr, cooled to room temperature, and 58.5 g (0.30 mole) 3,4-dichlorobenzyl chloride was added rapidly. The mixture was stirred and refluxed for 18 hr, cooled to 15°–20° and 2.0 ml $CH_3OH$ and 30 ml glacial acetic acid was added. With the temperature maintained at 10°–15°, the mixture was diluted with 800 ml $H_2O$. The toluene layer was separated and the aqueous layer was extracted with 300 ml toluene. The combined organic layers were washed with 500 ml $H_2O$, dried ($MgSO_4$), and concentrated to dryness in vacuo. The oily residue was washed 3 × 100 ml cold hexane and crystallized from 125 ml toluene to give 9.40 g (9.5%) of the product, m.p. 94°–99°. Further recrystallization from toluene gave the analytical sample, m.p. 99°–101°.

Anal. Calcd. for $C_{14}H_{13}Cl_2NO_4$: C, 50.93; H, 3.98; N, 4.24. Found: C, 50.74; H, 3.66; N, 4.15.

What is claimed:
1. Methyl 1-(3,4-dichlorobenzyl)-2,3-dioxoisonipecotate.

* * * * *